United States Patent [19]

Sato et al.

[11] Patent Number: 5,075,544
[45] Date of Patent: Dec. 24, 1991

[54] OPTICAL COLOR CHANGE DEVICE FOR DETECTING ELECTRICAL ABNORMALITY

[75] Inventors: Susumu Sato, Akita; Yoshihiro Togashi, Nagoya; Norio Ito, Nagoya; Koichi Ishii, Nagoya; Shinji Yasuda, Nagoya, all of Japan

[73] Assignees: Mitsubishi Denki Kabushiki Kaisha, Tokyo; Susumu Sato, Akita, both of Japan

[21] Appl. No.: 531,165

[22] Filed: May 31, 1990

[30] Foreign Application Priority Data

Nov. 24, 1989 [JP] Japan .................................. 1-305074

[51] Int. Cl.$^5$ ............................ G01J 3/50; G01J 1/48
[52] U.S. Cl. ................................... 250/226; 356/402; 422/86; 250/227.23
[58] Field of Search ......................... 250/227.23, 226; 356/402, 412, 437, 136, 135; 422/86, 87; 436/167

[56] References Cited

U.S. PATENT DOCUMENTS

| | | | |
|---|---|---|---|
| 3,998,591 | 12/1976 | Eckfeldt | 422/86 |
| 4,136,566 | 1/1979 | Chirstensen | 250/226 |
| 4,200,110 | 4/1980 | Peterson et al. | 256/412 |
| 4,471,186 | 9/1984 | Yoshioka | 422/86 |
| 4,560,248 | 12/1985 | Cramp et al. | 356/412 |
| 4,661,320 | 4/1987 | Ito et al. | 422/86 |
| 4,851,665 | 7/1989 | Pesavento et al. | 356/412 |
| 4,863,694 | 9/1989 | Kimmel et al. | 422/86 |

FOREIGN PATENT DOCUMENTS 1257185  7/1989  Canada ................................. 422/86

OTHER PUBLICATIONS

SF$_6$ Gasanalysis Technique and Its Application for Evaluation of Internal Condition in SF$_6$ Gas Equipment (IEEE, vol. PAS-100, No. 9, Sep. 1981).

Diagnostic Technique of Gas Insulated Substation by Partial Discharge Detection (IEEE, vol PAS-99, No. 4, Jul./Aug. 1980).

Primary Examiner—Davis L. Willis
Assistant Examiner—Michael Messinger
Attorney, Agent, or Firm—Oblon, Spivak, McClelland, Maier & Neustadt

[57] ABSTRACT

A device for detecting an electrical abnormality in an electrical device filled with insulating gas. A surface on a light reflecting prism placed within the electrical device carries a color indicator material. The color indicator material changes color when acidic gas is present. This gas is formed when an electrical abnormality such as a short circuit occurs in the presence of the insulator gas. A light source provides light to the prism which reflects light back having a color which varies according to the color of the color indicator material. The color of the reflected light is analyzed to determine if an electrical abnormality is present.

3 Claims, 2 Drawing Sheets

OPTICAL COLOR CHANGE DEVICE FOR DETECTING ELECTRICAL ABNORMALITY

BACKGROUND OF THE INVENTION

1. Field of the Invention

The present invention relates to an abnormality detecting device for detecting, for instance, a degree of deterioration or an abnormal state in an electric apparatus.

2. Discussion of the Background

Heretofore, a so called gas filled insulation apparatus wherein $SF_6$ gas or the like having excellent insulating, quenching performance is used as an insulating medium, has been used as a transformer, an interrupter, and for a bus bar or the like.

If an abnormal state takes place in such electric apparatus, and when arcing or corona discharge occurs or a short circuit takes place in an electric contact portion due to a fault in contact, such abnormality can not be easily detected from outside because electric components are covered a metallic casing. Accordingly, when abnormality takes place, it is necessary to take the following steps for the restoration of the electric apparatus: the operation of the electric apparatus is stopped; an insulating medium such as $SF_6$ is recovered; electric assemblies are dismantled; a fault component is detected, the fault component is repaired or replaced, and the electric apparatus is again assembled.

However, the dismantlement of the electric apparatus to inspect and find a fault component requires a large amount of work, there is difficulty in recovering the insulating medium, and it requires much time.

Therefore, a gas abnormality detecting device as in Japanese Unexamined Patent Publication No. 24844/1982 is proposed, for instance. However, the proposed device had a problem that it was difficult to obtain accurately information of abnormality.

SUMMARY OF THE INVENTION

It is an object of the present invention to provide an abnormality detecting device capable of finding an abnormal portion without dismantling the electric apparatus and capable of detecting an abnormal portion accurately.

According to the present invention, there is provided an abnormality detecting device which comprises a color indication material fixed in an insulating medium, a light source for emitting light which has a wavelength band region which changes due to the color reaction of the color indication material, a spectral decomposing device for decomposing light which is reflected by or transmitted through the color indication material from the light source and which is synthesized with the reflected or transmitted light, a sensor for detecting the light which has been subjected to spectral decomposition, and an operating means which operates the output of the sensor to thereby output a signal corresponding to the intensity of the light having each specified wavelength.

DESCRIPTION OF THE PREFERRED EMBODIMENT

An insulating gas such as $SF_6$ is used in an electric apparatus for the purpose of reducing the size of the apparatus and rendering the apparatus to be difficult to burn. In such electric apparatus, acidic gas such as HF, $SF_4$, $SOF_2$ or the like is produced when the insulating medium or an insulating material becomes deteriorate, or an abnormal state such as arcing, corona discharges or sparks take place.

A color indication material, which shows color reaction by the acidic gas (hereinafter, referred to as a color indication material), changes its color into a specified color due to the color indication material by an acidic reaction. In a sense of optics, the strength of reflectance of light and the strength of absorptivity of light of the color indication material change depending on the wavelength of light before and after the color reaction.

The present invention is accomplished on the basis of the above-mentioned principle. Namely, a color indication material is placed in an electric apparatus; light including a wavelength which changes by a color reaction inherent in the color indication material is irradiated from a light source to the color indication material, and the light reflected by the material or the light transmitted through the material is subjected to light wavelength analysis whereby the presence or the absence of the color reaction and the degree of the reaction can be detected.

The nature of $SF_6$ gas is neutral in a normal state and acidic gases are produced only when an abnormal state takes place, the presence or the absence of the deterioration of insulator and the degree of it can be detected in accordance with the presence or the absence of the color reaction. Accordingly, the color reaction can be applied to a diagnosis device for an electric apparatus.

An embodiment of the abnormality detecting device of the present invention will be described with reference to the drawings.

Figure 1:
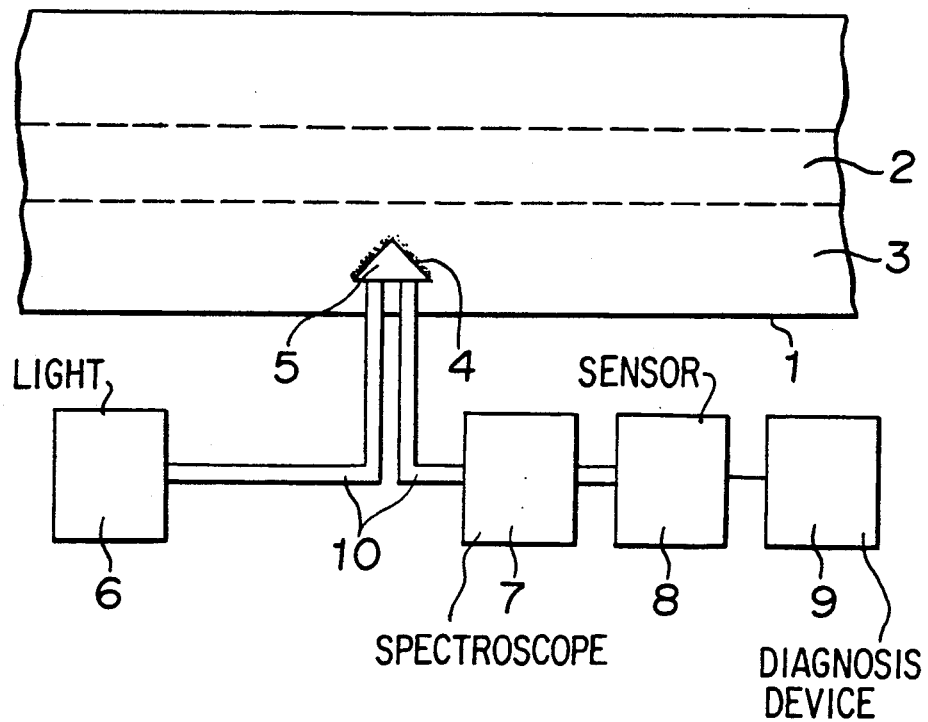
FIG. 1 is a diagram showing an embodiment of the abnormality detecting device according to the present invention.

In FIG. 1, a reference numeral 1 designates a grounded vessel which is used for a gas filled insulating apparatus, a numeral 2 designates a metallic conductor for the gas filled insulating apparatus, a numeral 3 designates $SF_6$ gas, a numeral 4 designates a color indication material, a numeral 5 designates a prism which fixes the color indication material in an insulating medium, a numeral 6 designates a light source such as a tungsten lamp which emits light including a wavelength band region which changes by a color reaction, a numeral 7 designates a spectroscope as a spectral decomposing device for light which reaches through the prism 5, a numeral 8 designates a photomultiplier tube (photomultiplier) as a sensor for the light which has been subjected to spectral decomposition, a numeral 9 designates a diagnosis device which operates the output of the photomultiplier 8 to determine the presence or the absence of deterioration or abnormality, and a numeral 10 designates optical fibers for transmitting light from the light source 6 to the spectroscope 7 through the prism 5.

Figure 2:
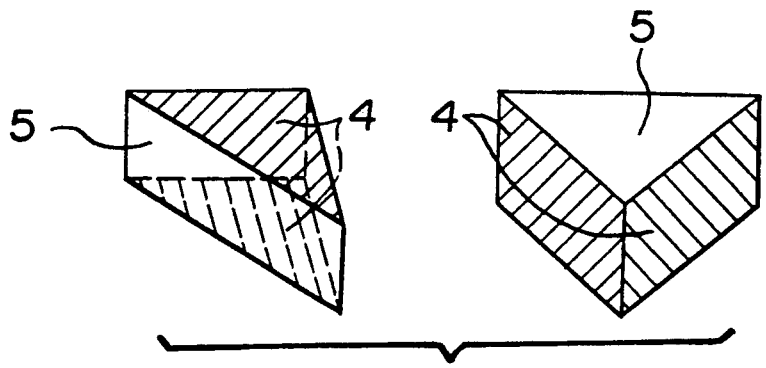
FIG. 2 is a diagram showing an embodiment of a color indication material as a structural element of the present invention and a substance to fix the color indication material in an insulating medium.

FIG. 2 is a diagram showing how the color indication material 1 is fixed to a surface or surfaces of the prism 5. Specifically, in case of using a crystal violet, a water solution of crystal violet is applied to the surface or surfaces of the prism and the prism is dried to thereby solidify the water solution.

The function of the abnormality detecting device of the present invention will be explained in accordance with FIG. 1.

Let's assume that the SF$_6$ gas is filled in the ground vessel 1 in a gas filled insulating apparatus and there takes place an arc discharge by any cause on the metallic conductor to which a high voltage is applied. The SF$_6$ gas is decomposed by the arc discharge whereby a product, which is represented by the following formula, is produced by the reaction with few amount of water contained in the apparatus:

$$(n/2)SF_6 + M \rightarrow (n/2)SF_4 + MF \qquad (1)$$

where M: a metal electrode and n: the chemical bond valence of the metal M.

Further, HF gas as a strong acidic gas is produced by the chemical reaction as follows:

$$SF_4 + H_2O \rightarrow SOF_2 + 2HF \qquad (2)$$

$$SOF_2 + H_2O \rightarrow SO_2 + 2HF \qquad (3)$$

Thus, by disposing a color indication material such as the crystal violet in the grounded vessel 1 so that there causes the color reaction of the color indication material to a strong acidic gas such as HF produced by the decomposition by discharge and the hydrolysis of SF$_6$, the color indication material exhibits a color reaction by the acidic gas. There has been known that the crystal violet exemplified here shows a blue or purple color as a alkaline color and an yellow color as an acidic color.

Thus, by detecting a change in the color indication material by the color reaction, it is possible to detect the decomposition of the SF$_6$ gas by arc discharging, namely, gas produced by the decomposition of the SF$_6$ gas. However, it was impossible to judge the deterioration of insulators or products resulted from the deterioration with high sensitivity through observation by naked eyes. The principal object of the present invention is to obtain a device capable of detecting with high sensitivity the color reaction of a color indication material to thereby detect the presence of gas produced by the decomposition of SF$_6$.

It is said that in a prism, the total reflection of an incident light is caused at wall surfaces of the prism. However, in fact, light leaks from the wall surfaces of the prism to the outside and the leaked light returns into the prism. In view of the fact, by attaching a color indication material on the wall surfaces of the prism, the light reflected from the prism show a spectrum corresponding to the color peculiar to the color indication material due to the absorption characteristic of light of the material.

When, for instance, an acidic gas is produced by arc discharging in an electric apparatus, there causes a change of color by the color reaction of a color indication material, and the spectrum of the reflected light is different from the spectrum as seen before the color reaction.

Figure 3:
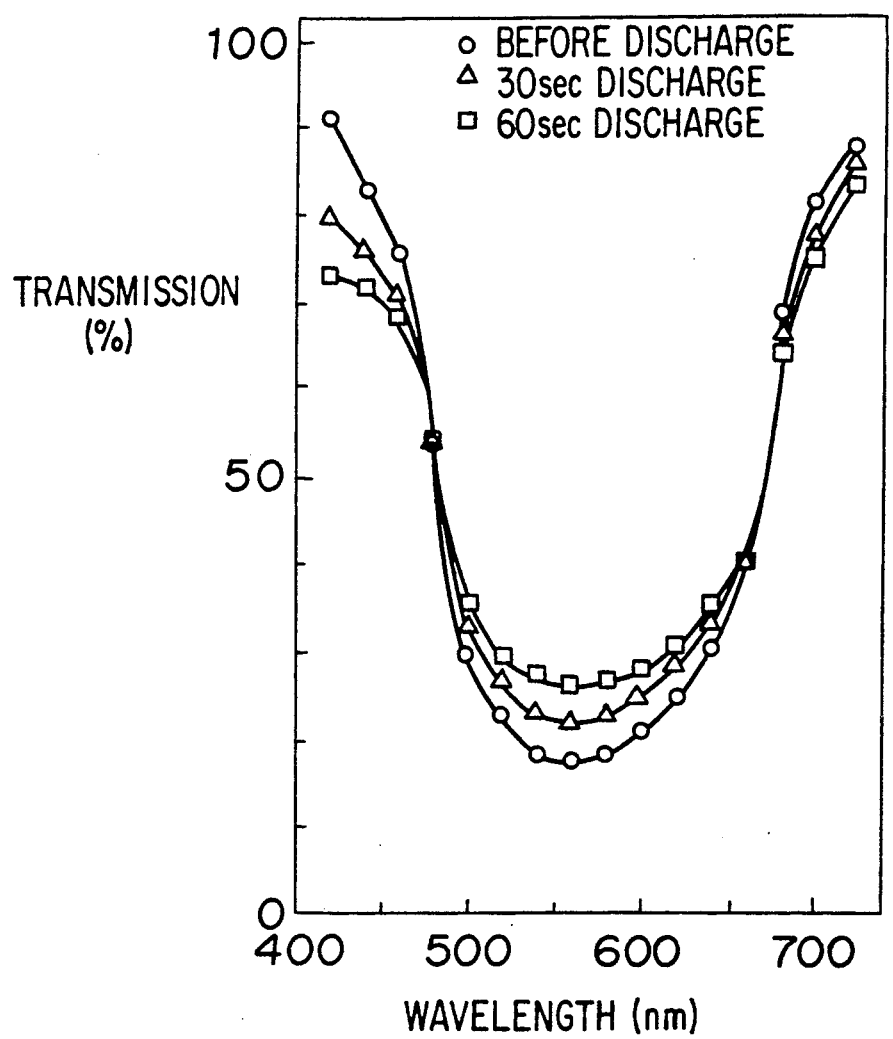
FIG. 3 is a diagram showing a result of experiments conducted according to the principle of the present invention.

FIG. 3 is a diagram showing a result of measurement of the spectral distribution of light reflected from a prism, in terms of a ratio of reflected light to incident light, i.e. transmission, before and after electric discharge wherein a simulation electrode and a prism on which a crystal violet is coated are placed in a SF$_6$ gas-filled deciccator, and electric discharges are forcibly caused at the simulation electrode. In FIG. 3, the abscissa represents wavelength (nm) and the ordinate represents transmission (%). FIG. 3 shows each spectral distribution to wavelengths before an electric discharge, and after a 30 sec electric discharge and a 60 sec electric discharge. As is apparent from FIG. 3, the transmission increases by electric discharges at or around a wavelength of 550 nm 18 600 nm, and the transmission decreases at a wavelength region shorter than about 450 nm and a wavelength region longer than about 700 nm. This implys that the crystal violet shows an yellow color as an acidic color. In accordance with the above-mentioned principle, the crystal violet shows a color reaction in an acidic gas atmosphere by the decomposition of SF$_6$ gas.

The function of the structural elements of the present invention is to detect the change of a spectrum to thereby determine deterioration or abnormality in insulators. The function of each of the elements will be described.

Light emitted from the light source 6 is introduced into the prism 5 through optical fibers 10. Light reflected from the prism 5 on which the color indication material 4 is coated is introduced into the spectroscope 7 through the optical fibers 10. A spectrum obtained by the spectroscope 7 is detected by the photomultiplier 8 to be converted into an electric signal. The diagnosis device 9 detects a wavelength which changes due to a color reaction, e.g. the intensity of light having a wavelength of about 550 nm ~600 nm when the crystal violet is utilized as the color indication material 4, and generates an alarm in the determination that an insulator becomes deteriorate or abnormal when the intensity of light having the wavelength reaches a predetermined value.

The diagnosis device 9 will be described in more detail. The fact that the color of the crystal violet as a color indication material changes to an yellow color by the reaction with an acidic gas implys that the reflectivity of light having a wavelength of about 550 nm ~600 nm increases. Detection by naked eyes is allowed only when the difference in reflectivity becomes significant. In order to detect the difference of reflectivity with high sensitivity, the following measures may be utilized, for instance. A white light is irradiated to a color indication material through a prism, and light reflected from the prism is subjected to spectral decomposition. In the spectrum of the reflected light, an attention is made to the greatly changed wavelength. When it is assumed that the output of the light source 6, i.e. the intensity of the white light is constant, the intensity of light reflected by the prism 5 on which the color indication material 4 is coated changes its wavelength depending on conditions of the color indication material 4. The diagnosis device 9 generates an alarm when the intensity of light at a wavelength around 550 nm reaches a predetermined level. The diagnosis device 9 can be constructed easily by applying electronics. In some cases it is possible for human to judge an electronic apparatus by observing the output in terms of wavelength of the photomultiplier 8.

In the above-mentioned embodiment, description has been made as to a technique of judging the deterioration or the abnormality by detecting the intensity of light at or around a wavelength of 550 nm ~600 nm. However, the following measures may be taken. For instance, by utilizing such tendency that the transmission of light is improved at or around a wavelength of 550 nm ~600 nm by the color reaction and the transmission is reduced at a wavelength region more than 700 nm, a ratio of the intensity of light at or around 550 nm ~600 nm to the intensity of light of more than 700 nm is used, and when the ratio reaches a predetermined level, an alarm may be generated, whereby it is possible to obtain a diagnosis for an electric apparatus with higher sensitivity than that as in the embodiment described before.

In FIG. 3, the transmission of light at 550 nm before the initiation of electric discharge and after 60 sec electric discharge are respectively 18% and 26%. There is the difference of about 1.4 times therebetween. On the other hand, the transmission of light at 700 nm under the above-mentioned conditions are respectively 82% and 76%. Accordingly, values in percentage of the transmission at 700 nm/the transmission at 550 nm before the initiation of electric discharge and after 60 sec electric discharge are respectively 82%/18% $\approx$ 4.6 and 76%/26% $\approx$ 2.9. Therefore there are the difference of about 1.6 times therebetween.

With respect to the abnormality detecting device as shown in FIG. 1, it is possible to diagnose an electric apparatus as to whether or not deterioration or abnormality occurs by arranging the abnormality detecting device of the present invention in a vessel filled with gas in the apparatus. In this case, it is unnecessary to dismantle the electric apparatus, and therefore, inspection can be made quickly, when any abnormality is found. A time for restoration is small.

In the above-mentioned embodiment, the crystal violet is used as a color indication material. However, another color indication material such as Bromocresol Purple may be used. Further, in the above-mentioned embodiment, the white light, which is obtainable by a tungsten lamp, a halogen lamp or the like, is used. However, an LD, an LED or the like may be used so long as a light source has a spectral distribution of light having a wavelength band region which changes by a color reaction.

In the above-mentioned embodiment, the spectroscope is used as a spectral decomposing device, and the photomultiplier tube is used as a photosensor. However, they may be combined.

In the above-mentioned embodiment, the prism is used as a fixing member for fixing a color indication material in an insulating medium whereby light entering into the prism through optical fibers is totally reflected and the reflected light is further transmitted through optical fibers. As such fixing means, a glass plate or a mirror may be used.

In FIG. 1, only the color indication material 4, the prism 5 and the optical fibers 10 may be arranged in the electric apparatus wherein a connector or connectors are provided at the optical fibers 10 so that the other structural elements are connected by using the connector or connectors when they are needed. Further, the device as shown in FIG. 1 is equipped in each electric apparatus so that a signal of each of the devices is observed.

Thus, in accordance with the present invention, deterioration or abnormality on an insulator in an electric apparatus which is filled with an insulating medium such as $SF_6$ can be detected with high sensitivity without dismantling the electric apparatus.

We claim:

1. A detecting device for an electrical abnormality in an electrical apparatus, said apparatus having a vessel containing a conductor and filled with an insulating gas, said device comprising:
   a light source for emitting light;
   a prism arranged within said vessel for receiving emitted light and producing reflected light;
   color indicator material applied to a surface of said prism, said color indicator material changing color in response to the presence of an acidic gas caused by a reaction of said insulating gas and an electrical abnormality, whereby the color of said reflected light is changed when said color indicator material changes;
   spectral decomposing means for separating said reflected light into selected colors;
   sensor means for detecting the intensity of light in the reflected beam for said selected colors and producing an output; and
   means for determining an abnormality according to the output of said sensor means.

2. The detecting device according to claim 1, wherein said emitted light and said reflected light are transmitted through optical fibers.

3. The abnormality detecting device according to claim 1, wherein the light source is a tungsten lamp emitting a white light.

* * * * *